United States Patent
Pe

(10) Patent No.: US 6,467,357 B1
(45) Date of Patent: Oct. 22, 2002

(54) CLAMPING APPARATUS AND METHOD FOR TESTING STRENGTH CHARACTERISTICS OF SHEETS

(75) Inventor: Zehong Yuan Pe, Duluth, GA (US)

(73) Assignee: Geostar Corp., Norcross, GA (US)

( * ) Notice: Subject to any disclaimer, the term of this patent is extended or adjusted under 35 U.S.C. 154(b) by 0 days.

(21) Appl. No.: 09/698,005

(22) Filed: Oct. 25, 2000

(51) Int. Cl.$^7$ .................................. G01N 3/20
(52) U.S. Cl. ............................ 73/859; 73/159
(58) Field of Search ................ 73/826, 831, 833, 73/837, 840, 856, 857, 859, 159

(56) References Cited

U.S. PATENT DOCUMENTS

| | | | |
|---|---|---|---|
| 3,383,864 A | 5/1968 | Turzillo | 61/38 |
| 3,686,873 A | 8/1972 | Vidal | 61/39 |
| 4,116,010 A | 9/1978 | Vidal | 405/262 |
| 4,324,508 A | 4/1982 | Hilfiker et al. | 405/284 |
| 4,447,935 A * | 5/1984 | Ausnit | 24/201 |
| 4,448,571 A | 5/1984 | Eckels | 405/284 |
| 4,661,023 A | 4/1987 | Hilfiker | 405/262 |
| 4,710,062 A | 12/1987 | Vidal et al. | 405/262 |
| 4,804,299 A | 2/1989 | Forte et al. | 405/285 |
| 4,824,293 A | 4/1989 | Brown et al. | 405/284 |
| 4,887,626 A * | 12/1989 | Dalo et al. | 135/119 |
| 4,914,876 A | 4/1990 | Forsberg | 52/169.4 |
| 5,028,172 A | 7/1991 | Wilson et al. | 405/286 |
| 5,033,912 A | 7/1991 | Vidal | 405/262 |
| 5,091,247 A | 2/1992 | Willibey et al. | 428/255 |
| 5,131,791 A | 7/1992 | Kitziller | 405/286 |
| 5,145,288 A | 9/1992 | Borcherdt | 405/284 |
| 5,156,496 A | 10/1992 | Vidal et al. | 405/262 |
| 5,163,261 A | 11/1992 | O'Neill | 52/610 |
| 5,277,520 A | 1/1994 | Travis | 405/128 |
| 5,417,523 A | 5/1995 | Scales | 405/284 |
| 5,419,092 A | 5/1995 | Jaecklin | 52/562 |
| 5,595,460 A | 1/1997 | Miller et al. | 405/284 |
| 5,788,420 A | 8/1998 | Scales | 405/262 |
| 5,800,095 A | 9/1998 | Egan | 405/262 |
| 5,800,097 A | 9/1998 | Martin | 405/284 |
| 5,816,749 A | 10/1998 | Bailey, II | 405/286 |
| 5,988,941 A * | 11/1999 | Sargent et al. | 405/3 |
| 6,019,550 A | 2/2000 | Wrigley et al. | 405/262 |
| 6,039,520 A * | 3/2000 | Cheng | 410/106 |
| 6,224,295 B1 | 5/2001 | Price et al. | 405/262 |

OTHER PUBLICATIONS

Designing with Geosynthetics, Koerner, Robert M., Prentice–Hall, Inc., Englewood Cliffs, NJ 07632, 3$^{rd}$ ed.—p. 37–42; 192–199; 328–351.

Safe slope reinforcement and stable embankment construction (undated).

* cited by examiner

Primary Examiner—Max Noori
(74) Attorney, Agent, or Firm—Baker, Donelson Bearman & Caldwell

(57) ABSTRACT

A holding clamp for use in a testing apparatus for determining tensile and sheer strength characteristics of a reinforcement sheet. The holding clamp defines a channel having at least two adjacent bearing surfaces and an opening to an exterior surface. An elongate clamping bar conforming in cross-sectional shape at least relative to the pair of adjacent bearing surfaces is received within the channel with an end portion of the reinforcement sheet overwrapping the clamping bar and a portion of the reinforcement sheet extends outwardly through the opening for securing in the testing apparatus. A loading mechanism moves the clamp to load the reinforcement sheet, whereby the tensile or sheer strength characteristics can be determined. A method of clamping an end of a reinforcement sheet to be tested for tensile or sheer strength characteristics is disclosed for a testing apparatus.

24 Claims, 2 Drawing Sheets

CLAMPING APPARATUS AND METHOD FOR TESTING STRENGTH CHARACTERISTICS OF SHEETS

TECHNICAL FIELD

The present invention relates to testing equipment for determining strength characteristics of sheets. More particularly, the present invention relates to clamps for testing equipment, which clamps uniformly grip end portions of sheets to be loaded for testing of tensile or shear strength characteristics.

BACKGROUND OF THE INVENTION

Elongate sheet materials are commonly used in mechanically stabilized earth retaining walls. The retaining walls are constructed with modular precast concrete members in the form of blocks or panels that stack on top of each other to create the vertical facing of the wall. The sheet materials extend laterally from connections with the blocks in the wall. The sheet materials are construction devices used to reinforce earthen slopes retained from slippage by the retaining wall, particularly where changes in elevations occur rapidly, for example, site developments with steeply rising embankments. These embankments must be secured against collapse or failure to protect persons and property from possible injury or damage caused by the slippage or sliding of the earthen slope.

Many designs for earth retaining walls exist today. Wall designs must account for lateral earth and water pressures, the weight of the wall, temperature and shrinkage effects, and earthquake loads. The design type known as mechanically stabilized earth retaining walls employ either metallic or polymeric tensile reinforcements in the soil mass. The tensile reinforcements extend laterally of the wall formed of facing units, typically precast concrete members, blocks, or panels stacked together. The tensile reinforcements connect the soil mass to the blocks that define the wall. The blocks create a visual vertical facing for the reinforced soil mass. The polymeric tensile reinforcements typically used are elongated lattice-like structures often referred to as grids. These are stiff polymeric extrusions. The grids have elongated ribs which connect to transversely aligned bars thereby forming elongated apertures between the ribs. Tensile reinforcements other than grids have been developed for use with mechanically stabilized earth retaining walls. These other tensile reinforcements are flexible reinforcement sheets, including large open-grid woven lattices and small aperture woven lattices, as well as woven textile sheets.

The specifications for earth retaining walls are based upon the strength of the interlocking components and the load created by the backfill. Once the desired wall height and type of ground conditions are known, the number of sheets, the vertical spacing between adjacent sheets, and lateral positioning of the sheets is determined, dependent upon the load capacity of the interlocking components.

To design an earth retaining wall, various strengths of the sheet material must be known in order to meet the specification for the site requirements. Sheet materials are tested to determine the tensile strength and also to test shear resistance to pullout. Tensile strength testing considers whether the sheet itself will fail by tearing. Pull-out resistance considers whether the sheet insufficiently engages the backfill material and thus slips laterally through the backfill. Testing of sheet materials is typically accomplished by independent labs. Design engineers use the test data to select the type and supplier of sheets for retaining wall projects.

During testing, at least one end of the sheet is secured by a clamp. There are a number of different types of clamps. Compression clamps secure the test sheet between two elongate members to which a compression loading is applied. Epoxy clamps use molding epoxy to form a build-up body around the test specimen. Bolts pass through the epoxy body for connecting to the test apparatus. Split wedge clamps apply a gripping force on the test sheet passing through a split wedge body. Roller grips wrap opposing portions of the test sheet around rollers.

For tensile strength testing, the opposing end of the sheet is secured by another clamp. Loading is then applied to the test sheet. A load cell measures the amount of force being applied to the test sheet. As the loading force continues to increase, the sheet ultimately fails. The tensile strength of the sheet is recorded.

Pullout testing examines the resistance of the sheet to pulling out from backfill material or from between the blocks in the wall. For backfill shear resistance testing, a portion of the test sheet is embedded with backfill material in a soil box. For normal load (block wall pullout), the sheet is placed between blocks used in constructing the wall. Loading is applied to move the clamp laterally. When the sheet pulls out from the soil box or from between the blocks, the shear resistance is recorded.

One drawback to some of these testing devices is that the loading is concentrated at the point of attachment. Accordingly, the failure of the sheet sometimes occurs at the point of attachment, rather than the failure occurring in an intermediate portion of the sheet. The testing therefore, does not provide a true measure of the tensile strength of the sheet material, but rather provides an indication of the strength at a concentrated point.

In some tests, the grip by the clamp on the test sheet slips. The higher the loading, the more likely the incidence of slippage in the clamp. This of course does not accurately test the sheet.

Also, clamps for some testing devices are time consuming to assemble and attach to the test sheet. Epoxy clamps particularly require a curing period, and the epoxy materials are single use only which increases costs. Split wedge clamps are awkward to assemble with the test sheet.

Accordingly, there is a need in the art for an improved clamp for use in testing apparatus for determining the tensile and pull-out resistance strengths of sheets. It is to such that the present invention is directed.

BRIEF SUMMARY OF THE INVENTION

The present invention meets the need in the art by providing a holding clamp for sheet testing apparatus, which holding clamp engages an end portion of a reinforcement sheet to be tested for tensile or pull-out strengths. The holding clamp defines a channel having at least two adjacent bearing surfaces and an opening between the bearing surfaces to an exterior surface. The channel receives an elongate clamping bar that conforms in cross-sectional shape at least relative to the pair of adjacent bearing surfaces. An end portion of the test sheet wraps around the clamping bar, which is received in the channel with the sheet extending laterally through the opening. Depending on the testing, the opposing end of the sheet is secured by another holding device or by the backfill material or blocks. A loading device applies an increasing load to the sheet through the clamp for determining the strength of the sheet. The clamping bar mechanically engages the bearing surfaces of the channel to distribute the tensile loading to the bearing surfaces of the block.

In another aspect, the present invention provides a method of securing a reinforcement sheet with a clamp for use in a testing apparatus for determining a tensile or pull-out strengths of the reinforcement sheet, comprising the steps of:

(a) providing a holding clamp that defines a channel extending between opposing sides and having at least two adjacent bearing surfaces and an opening to an exterior surface thereof between the bearing surfaces;

(b) sliding a clamping bar overwrapped with an end portion of a sheet to be tested for tensile or pull-out strength along the channel with a portion of the reinforcement sheet extending outwardly through the opening, the clamping bar conforming in cross-sectional shape at least relative to the pair of adjacent bearing surfaces defined in the channel;

(c) securing an opposing end of the reinforcement sheet; and (d) loading the reinforcement sheet through the clamp with an increasing force, whereby the clamping bar, being wrapped by the reinforcement sheet that is loaded with the increasing force, mechanically engages the two bearing surfaces of the channel such that the tensile loading on the reinforcement sheet is applied to the two bearing surfaces in the block for measuring the strength of the reinforcement sheet.

Objects, advantages and features of the present invention will become apparent from a reading of the following detailed description of the invention and claims in view of the appended drawings.

DETAILED DESCRIPTION OF THE PREFERRED EMBODIMENTS

Figure 1:
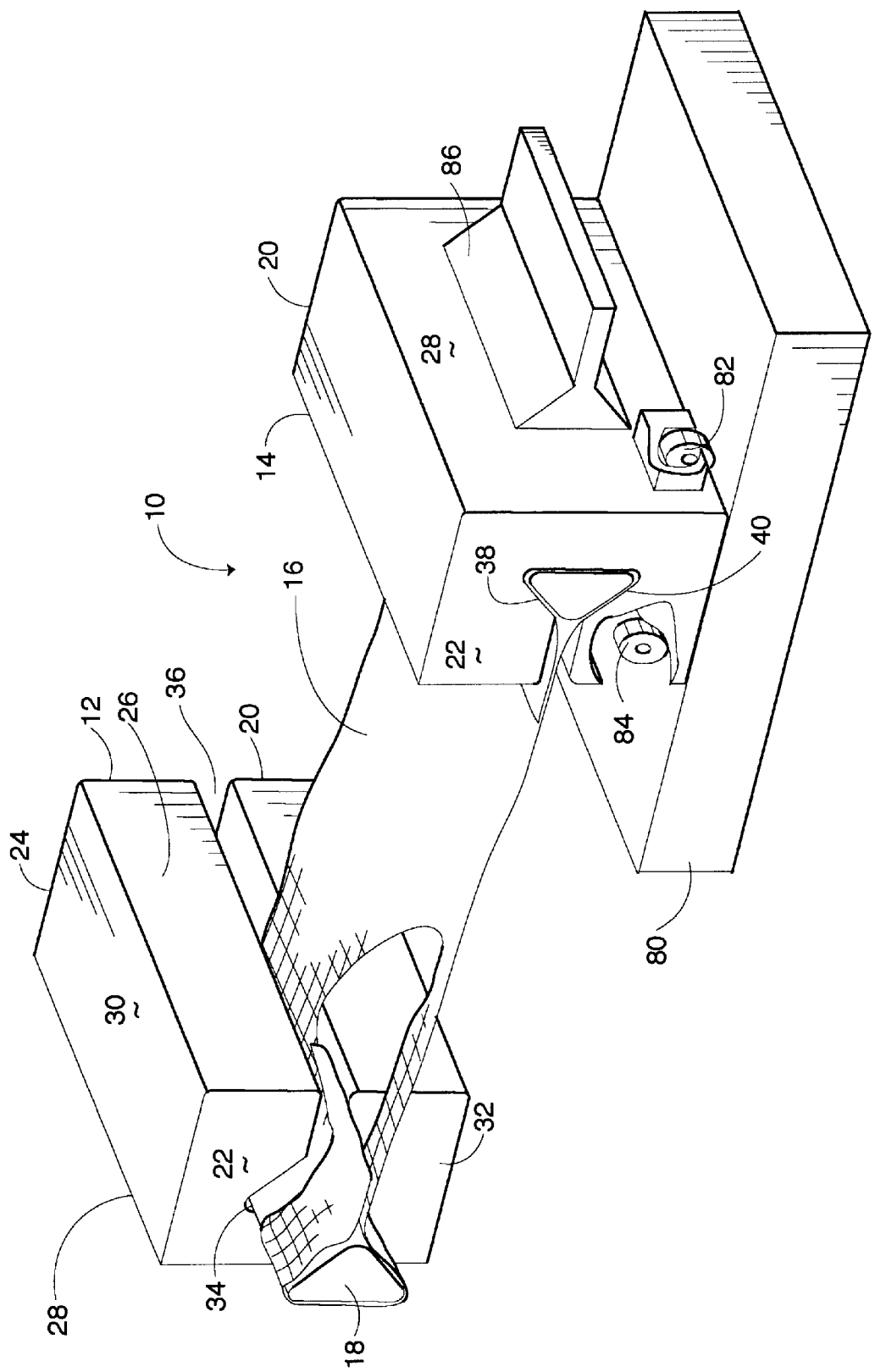
FIG. 1 illustrates a perspective cut-away view of a clamp according to the present invention useful in a sheet testing apparatus.

Referring now in more detail to the drawings in which like parts have like identifiers, FIG. 1 is a perspective view of a clamp 12 according to the present invention illustrated with a testing apparatus 10 for determining tensile strength of a reinforcement sheet 16 secured in the testing apparatus. The illustrated testing apparatus 10 uses a pair of opposed holding clamps 12, 14. In this embodiment, the clamp 14 is similar to the clamp 12. The reinforcement sheet 16 extends between the holding clamps 12, 14 for testing the tensile strength of the reinforcement sheet, as discussed below. The reinforcement sheet 16 is held in the clamp 12 by a clamping bar 18. The reinforcement sheet 16 overwraps the clamping bar 18 which extends through a channel 34 in the holding clamp 12. The reinforcement sheet 16 extends outwardly through an opening of the holding clamp 12. The clamping bar 18 communicates the tensile loading on the reinforcement sheet 16 to the holding clamp 12.

In the illustrated testing apparatus 10, the holding clamps 12, 14 are each defined by a block body 20 adapted for engaging the reinforcement sheet 16. The block body 20 is defined by opposing side walls 22, 24, opposing front face 26 and back face 28, and opposing top and bottom sides 30, 32. The block body 20 defines a channel 34 extending between the opposing sides 22, 24. In a preferred embodiment, the channel 34 defines a substantially triangular shape in cross-sectional view. In a preferred embodiment, the triangular channel 34 is substantially equilateral. The block body 20 defines an opening 36 in the face 26. The edges of the opening to the face 26 are preferably radiused or tapered. The channel 34 defines a pair of bearing surfaces 38, 40, for a purpose discussed below. The opening 36 is preferably between the two bearing surfaces 38, 40.

The holding clamps 12, 14 are identical and can be connected to a base (platform) and a moving cross-head, respectively. Connections to a specific testing machine can be easily accomplished. Accordingly, one end of the sheet is fixed while the other end is secured to a movable holder.

In the illustrated embodiment, the holding clamp 14 is supported on a base 80. The holding clamp 14 includes rollers 82, 84 on opposing sides of the block, two of which are illustrated. The rollers 82, 84 allow the holding clamp 14 to move between a first position towards the opposing holding clamp 12 to a second position away from the holding clamp 12. The back face 28 of the holding clamp 14 attaches by a connector 86 to a cross-head of a testing machine (not illustrated), for moving the holding clamp 14 between the first and second positions.

Figure 2:
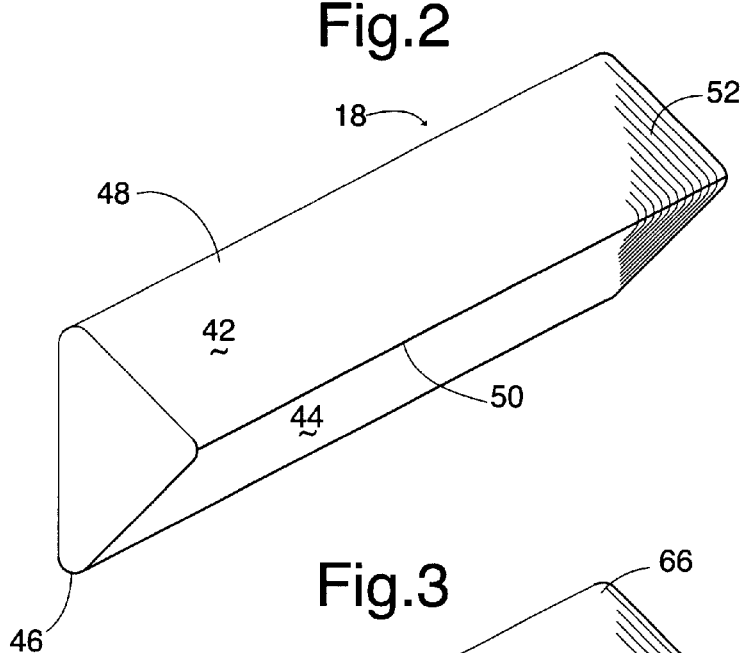
FIG. 2 illustrates in perspective view an embodiment of a clamping bar according to the present invention for use with the testing apparatus illustrate in FIG. 1.

FIG. 2 is a perspective view of an embodiment of the clamping bar 18 according to the present invention. The clamping bar 18 is received in the channel 34 of the block body 20, as discussed below, for communicating the tensile loading from the reinforcement sheet 16 to the bearing surfaces 38, 40 of the block body. In cross-sectional view, the clamping bar 18 defines a substantially triangular shape for conformingly being received within the channel 34. At least two surfaces 42, 44 conform to the bearing walls 38, 40. In a preferred embodiment, the clamping bar 18 defines an equilateral triangle to facilitate installation in the channel 34. The clamping bar 18 defines three apexes 46, 48, and 50. In the illustrated embodiment, the apexes 46, 48, and 50 define radiused ends. For example, the clamping bar 18 in one embodiment has a length of twelve inches, and equilateral sides of approximately 1.5 inches reduced slightly to accommodate the apex radiuses of 0.1094 inches. In one embodiment, an exterior surface of the clamping bar 18 has texturing generally 52, such as spaced-apart grooves and ridges, cross-hatching, roughened projections and recessed areas and the like, for a purpose discussed below. The clamping bar 18 is preferably formed of a high strength material, such as plastic or metal.

Figure 3:
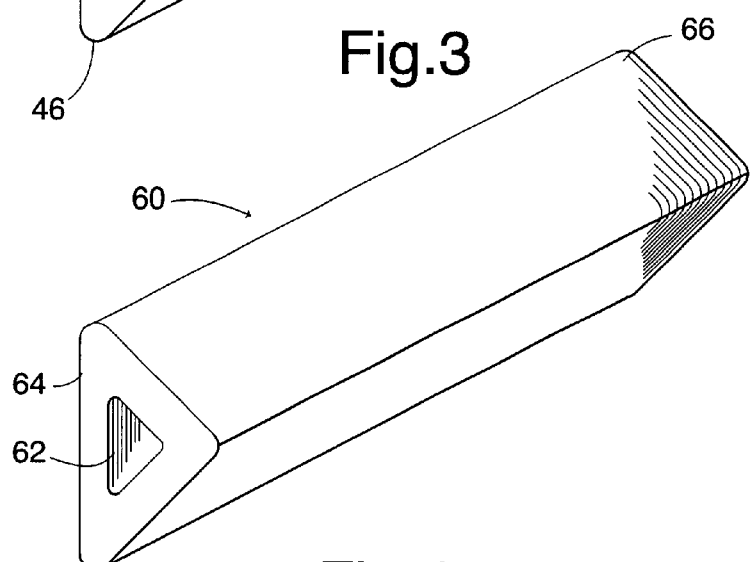
FIG. 3 illustrates in perspective view an alternate embodiment of the clamping bar illustrated in FIG. 2.

FIG. 3 is a perspective view of an alternate embodiment of a clamping bar 60. In this embodiment, the clamping bar 60 defines a cavity 62 extending between opposing distal ends 64, 66 along a longitudinal axis. In the illustrated embodiment, the cavity 62 conforms in cross-sectional shape to the cross-sectional shape of the clamping bar 60.

Figure 4:
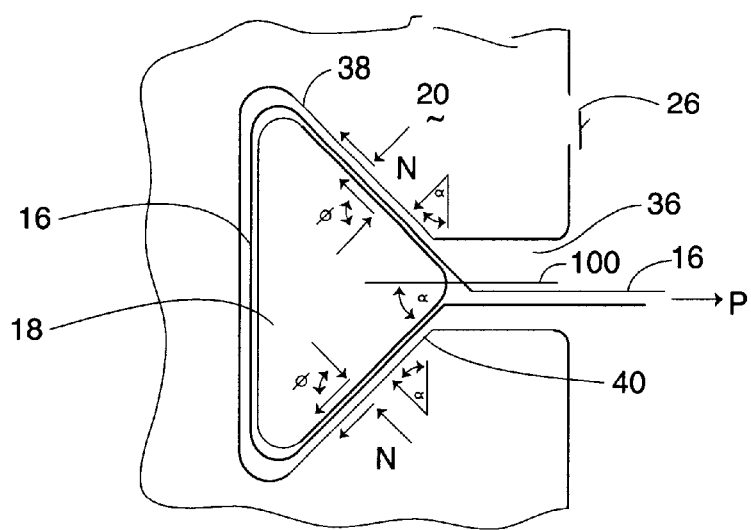
FIG. 4 illustrates a design concept for the present invention.

With reference to FIG. 1, the present invention provides a self-locking clamping bar 18 for securing laterally extending geosynthetic tie-back reinforcement sheet 16 to a clamp block 20 in a testing appartus 10. In the preferred embodiment, the reinforcement sheet 16 extends laterally from the block body 20 on a cross-sectional transverse center line of the clamping bar 18. With reference to FIG. 4, one of the apexes of the clamping bar 18 bearingly inserts into the opening 36 between the opposing bearing surfaces 38, 40. A reinforcement sheet 16 that is not aligned with a center line 100 tends to cause the clamping bar 18 to twist, which is not preferred. It is preferred that the normal loading arising from the friction between the clamping bar 18 and the respective bearing surfaces of the channel are equal.

The clamp 14 is connected to the moving cross-head of a typical tensile test machine. The clamp 12 is connected to a platform of a typical tensile test machine. The reinforcement sheet (test specimen) is loaded when the cross-head moves away from the base.

With reference to FIG. 4, a design for the testing apparatus 10 may be described as follows, where:

P is the pull-out loading for the reinforcement sheet 16, which equals the resisting force of the friction between the clamping bar 18 and the bearing surfaces 38, 40.

N is the normal loading between the bearing surface 38, 40 and the clamping bar 18.

α is the angle between the normal load N and a perpendicular line to the reinforcement sheet 16.

φ is the friction angle at the planar interface between the reinforcement sheet 16 and the clamping bar 18. This angle controls the self-locking attribute of the apparatus of the present invention.

The present invention is described by the following equation:

$$P = 2N \sin \alpha \quad \text{(Eq.1)}$$

The mobilized peak pull-out resistance is represented by the frictional load between the reinforcement sheet 16 and the bearing surfaces 38, 40 of the channel 34 and between the reinforcement sheet 16 and the clamping bar 18.

The tensile loading on the reinforcement sheet 16 accordingly is resisted by four surfaces of frictional loading. This is described by the following equation:

$$P = 4N \tan \phi \quad \text{(Eq.2)}$$

Combining equations one and two shows:

$$2N \sin \alpha = 4N \tan \phi \quad \text{(Eq. 3)}$$

which reduces to $$\sin \alpha = 2 \tan \phi \quad \text{(Eq. 4)}$$

Generally, higher values of the angle φ provide increased self-locking capability of the clamping bars 16.

For example, assume that a equals 30°. In order to have a reinforcement sheet 16 fully locked in the block body 20 by the clamping bar 18, $$\phi \geq \text{arc tan (sin alpha/2), or arc tan (0.5/2)}.$$

Accordingly, φ ≧ 14°.

It is noted that the friction angle φ between a clamping bar 18 and a reinforcement sheet 16 is likely greater than the computed 14°, thereby achieving the self-lock pull-out resistance of the present invention. In the event that sliding failure mode occurs, the angle of α can be reduced, and thus a smaller φ will meet the requirements for self-lock securing of the reinforcement sheet 16 to the block body 20 by the clamping bar 18.

The clamp 14 is connected to the moving cross-head of a typical tensile test machine. The clamp 12 is connected to platform of a typical tensile test machine. The reinforcement sheet (test specimen) is loaded when the cross-head moves away from the base.

With reference to FIG. 1, the holding clamps 12, 14 are used in the testing apparatus 10. Distally opposing ends of the reinforcement sheet 16 are gripped in the holding clamps 12, 14. This is accomplished by first moving the holding clamp 14 towards the holding clamp 12 for placing the reinforcement sheet 16 in the testing apparatus 10. An end portion of the reinforcement sheet 16 is wrapped around one of the clamping bars 18. The clamping bar 18 with the wrapped reinforcement sheet 16 then is slidably inserted into the channel 34 of the holding clamp 12. The lateral portion of the reinforcement sheet 16 is slidably moved through the opening 36 and extended to the second holding clamp 14. The opposing distal end of the reinforcement sheet 16 wraps over another of the clamping bars 18. This second clamping bar is then slidably received in the holding clamp 14. As illustrated in FIG. 1, portions of the opposing ends of the holding sheets extend outwardly of the openings 36 in the holding clamps 12, 14. The respective clamping bars 18 are then wedged in the opening 36 of the holding clamps 12, 14. This is accomplished by grasping the extended portion and the main portion of the reinforcement sheet 16 and pulling towards the opposing holding clamp in order to wedge the clamping bar 18 against the bearing surfaces 38, 40 of the respective holding clamp.

Tensile loading is then applied to the reinforcement sheet 16. In the illustrated embodiment, the second clamp 14 is moved in a direction away from the first holding clamp 12. In the illustrated embodiment, the holding clamp 14 is moved by operation of a hydraulic cylinder. The rollers 82, 84 facilitate the travel of the holding clamp 14 between the first position towards the opposing holding clamp 12 and the second position away from the holding clamp. The moving-away of the holding clamp 14 applies increasing tensile load on the reinforcement sheet 16. The tensile loading on the reinforcement sheet 16 impels the clamping bars 18 to wedgingly engage the respective openings 36 between the bearing surfaces 38, 40 of the channels 34. The surfaces 42, 44 of the clamping bar 18 engage the bearing surfaces 38, 40. This locks the reinforcement sheet 16 in place within the holding clamps 12, 14 together with the clamping bar 18 in the block body 20. The tensile loading is monitored to determine the force required to cause the reinforcement sheet 16 to fail. It is noted that the illustrated embodiment of the testing apparatus 10 is horizontal, and that the clamps 12, 14 also work in the testing apparatus that is vertically oriented.

It is to be appreciated that one clamp 12 is gainfully used with a shear resistance testing apparatus (not illustrated), in which a portion of the test sheet 16 is embedded in a soil box of backfill material or between blocks for normal loading to test pull-out resistance.

It is thus seen that the present invention as disclosed herein provides a testing apparatus for determining the tensile strength of elongate reinforcement sheets particularly useful in constructing earth retaining walls. While this invention has been described in detail with particular reference to the preferred embodiments thereof, the principles and modes of operation of the present invention have been described in the foregoing specification. The invention is not to be construed as limited to the particular forms disclosed because these are regarded as illustrative rather than restrictive. Moreover, modifications, variations and changes may be made by those skilled in the art without departure from the spirit and scope of the invention as described by the following claims.

What is claimed is:

1. A clamp for use in holding a reinforcement sheet in testing apparatus for determining strength characteristics of the reinforcement sheet, comprising:

a body for engaging an end portion of a reinforcement sheet to be tested for strength characteristics, the body defining a channel having at least two adjacent bearing surfaces and an opening between the bearing surfaces to an exterior surface of the body; and an elongate clamping bar conforming in cross-sectional shape at least relative to the pair of adjacent bearing surfaces defined in the channel for being received within the channel, whereby the clamping bar, being wrapped by a portion of the reinforcement sheet and received in the channel with the reinforcement sheet extending laterally through the opening and for being secured in a testing apparatus, mechanically engages the bearing surfaces of the channel to distribute tensile loading to the bearing surfaces.

2. The clamp as recited in claim 1, wherein the channel defines a triangular shape in cross-sectional view.

3. The clamp as recited in claim 2, wherein the clamping bar defines a triangular shape in cross-sectional view.

4. The clamp as recited in claim 3, wherein the clamping bar defines a second channel extending along a longitudinal axis thereof.

5. The clamp as recited in claim 3, wherein the clamping bar defines textured exterior surfaces.

6. The clamp as recited in claim 1, wherein the channel and the clamping bar define equilateral triangles in cross-sectional view.

7. The clamp as recited in claim 6, wherein the clamping bar defines a second channel extending along a longitudinal axis thereof.

8. The clamp as recited in claim 6, wherein the clamping bar defines textured exterior surfaces.

9. The clamp as recited in claim 1, wherein the clamping bar defines textured exterior surfaces.

10. The clamp as recited in claim 1, wherein the clamping bar defines a second channel extending along a longitudinal axis thereof.

11. A testing apparatus for determining a tensile strength of a reinforcement sheet, comprising:
a first holding clamp for engaging an end portion of a reinforcement sheet to be tested for tensile strength and defining a channel having at least two adjacent bearing surfaces and an opening between the bearing surfaces to an exterior surface of the first holding clamp;
a second holding clamp adapted for engaging an opposing end portion of the reinforcement sheet;
a loading device for applying an increasing tensile loading to the reinforcement sheet; and
an elongate clamping bar conforming in cross-sectional shape at least relative to the pair of adjacent bearing surfaces defined in the channel for being received within the channel,
whereby the clamping bar, being wrapped by a portion of the reinforcement sheet and received in the channel with the reinforcement sheet extending laterally through the opening for engaging the opposing end to the second holding clamp and loaded by the loading device, mechanically engages the bearing surfaces of the channel to distribute the tensile loading to the bearing surfaces.

12. The testing apparatus as recited in claim 11, wherein the loading device comprises means for moving the first holding clamp and the second holding clamp relatively apart.

13. The testing apparatus as recited in claim 12, wherein the means for moving comprises a hydraulic cylinder attached to the second holding clamp for moving the second holding clamp in a first direction to load the reinforcement sheet.

14. The testing apparatus as recited in claim 11, wherein the channel defines a triangular shape in cross-sectional view.

15. The testing apparatus as recited in claim 14, wherein the clamping bar defines a triangular shape in cross-sectional view.

16. The testing apparatus as recited in claim 15, wherein the clamping bar defines a second channel extending along a longitudinal axis thereof.

17. The testing apparatus as recited in claim 15, wherein the clamping bar defines textured exterior surfaces.

18. The testing apparatus as recited in claim 11, wherein the channel and the clamping bar define an equilateral triangle in cross-sectional view.

19. The testing apparatus as recited in claim 18, wherein the clamping bar defines a second channel extending along a longitudinal axis thereof.

20. The testing apparatus as recited in claim 18, wherein the clamping bar defines textured exterior surfaces.

21. The testing apparatus as recited in claim 11, wherein the clamping bar defines textured exterior surfaces.

22. The testing apparatus as recited in claim 11, wherein the clamping bar defines a second channel extending along a longitudinal axis thereof.

23. A method of securing a reinforcement sheet in a clamp for a testing apparatus for determining a strength characteristic of the reinforcement sheet, comprising the steps of:
(a) providing a holding clamp that defines a channel extending between opposing sides and having at least two adjacent bearing surfaces and an opening to an exterior surface thereof between the bearing surfaces;
(b) sliding a clamping bar overwrapped with an end portion of a reinforcement sheet to be tested for a strength characteristic along the channel with a portion of the reinforcement sheet extending outwardly through the opening, the clamping bar conforming in cross-sectional shape at least relative to the pair of adjacent bearing surfaces defined in the channel; and
(c) securing an opposing end of the reinforcement sheet,
whereby the clamping bar, being wrapped by the reinforcement sheet that is loaded with an increasing tensile force, mechanically engages the two bearing surfaces of the channel such that the tensile loading on the clamping bar is distributed to the bearing surfaces for measuring the strength characteristic of the reinforcement sheet.

24. A method of securing a reinforcement sheet in a testing apparatus for determining a tensile strength of the reinforcement sheet, comprising the steps of:
(a) providing a first holding clamp that defines a channel extending between opposing sides and having at least two adjacent bearing surfaces and an opening to an exterior surface thereof between the bearing surfaces;
(b) sliding a clamping bar overwrapped with an end portion of a reinforcement sheet to be tested for tensile strength along the channel with a portion of the reinforcement sheet extending outwardly through the opening, the clamping bar conforming in cross-sectional shape at least relative to the pair of adjacent bearing surfaces defined in the channel; and
(c) attaching a second opposing end of the reinforcement sheet to a second holding clamp,
whereby the clamping bar, being wrapped by the reinforcement sheet that is loaded with an increasing tensile force, mechanically engages the two bearing surfaces of the channel such that the tensile loading on the clamping bar is distributed to the bearing surfaces for measuring the tensile strength at failure of the reinforcement sheet.

* * * * *